US010307064B2

(12) United States Patent
Da Silva et al.

(10) Patent No.: US 10,307,064 B2
(45) Date of Patent: Jun. 4, 2019

(54) METHOD AND DEVICE FOR LOCATING AT LEAST ONE TARGET IN AN ELECTROMAGNETICALLY ABSORBENT ENVIRONMENT

(71) Applicants: Centre National de la Recherche Scientifique, Paris (FR); Ecole Centrale de Marseille, Marseilles (FR); Universite d'Aix Marseille, Marseilles (FR)

(72) Inventors: Anabela Da Silva, Marseilles (FR); Serge Mensah, Marseilles (FR)

(73) Assignees: Centre National de la Recherche Scientifique, Parid (FR); Ecole Centrale de Marseille, Marseilles (FR); Universite d'Aix Marseille, Marseilles (FR)

( * ) Notice: Subject to any disclaimer, the term of this patent is extended or adjusted under 35 U.S.C. 154(b) by 692 days.

(21) Appl. No.: 14/888,611

(22) PCT Filed: Mar. 24, 2014

(86) PCT No.: PCT/FR2014/050679
§ 371 (c)(1),
(2) Date: Nov. 2, 2015

(87) PCT Pub. No.: WO2014/177779
PCT Pub. Date: Nov. 6, 2014

(65) Prior Publication Data
US 2016/0058296 A1 Mar. 3, 2016

(30) Foreign Application Priority Data
May 2, 2013 (FR) ..................... 13 54072

(51) Int. Cl.
*A61B 8/00* (2006.01)
*G01N 21/17* (2006.01)
*A61B 5/00* (2006.01)

(52) U.S. Cl.
CPC .......... *A61B 5/0095* (2013.01); *A61B 5/0093* (2013.01); *G01N 21/1702* (2013.01);
(Continued)

(58) Field of Classification Search
CPC . A61B 2576/00; A61B 5/0093; A61B 5/0095; A61B 5/0059; A61B 8/00; G01N 21/1702
See application file for complete search history.

(56) References Cited

U.S. PATENT DOCUMENTS 5,891,158 A * 4/1999 Manwaring ............ A61B 90/14
600/102
6,490,470 B1 * 12/2002 Kruger ................. A61B 5/0095
600/407
(Continued)

FOREIGN PATENT DOCUMENTS

EP 1 935 346 6/2008
WO 2011 096198 8/2011

OTHER PUBLICATIONS

Sergey A. Ermilov, et al., "Laser optoacoustic imaging system for detection of breast cancer" Journal of Biomedical Optics, vol. 14, No. 2, 2009, 14 Pages.
(Continued)

*Primary Examiner* — Baisakhi Roy
(74) *Attorney, Agent, or Firm* — Oblon, McClelland, Maier & Neustadt, L.L.P.

(57) ABSTRACT

A method for locating at least one target, in an electromagnetically absorbent environment, includes: emitting at least one electromagnetic excitation signal from a source; receiving, by an acoustic sensor, an acoustic signal from emission
(Continued)

Figure 1:
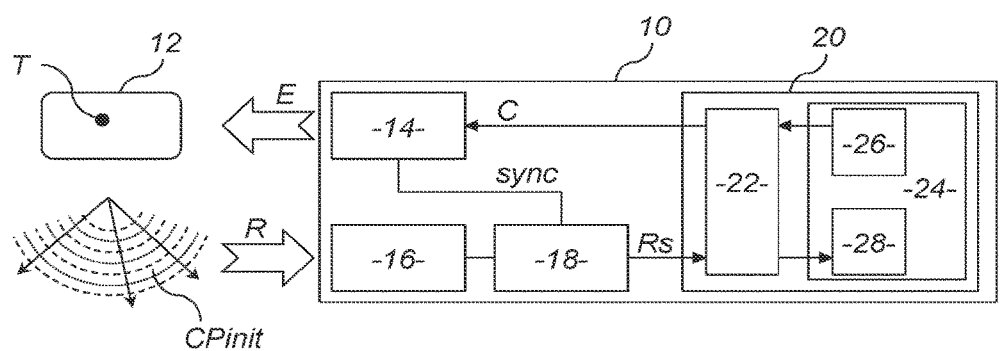

of the excitation signal; detecting, in the received acoustic signal, a first time of receipt of a first response to the excitation signal from an acoustic disturbance caused by electromagnetic heterogeneity of the target in the environment; estimating a first distance between the target and the acoustic sensor using the first time of receipt; detecting, in the same received acoustic signal, a second time of receipt of a second response to the excitation signal from an acoustic disturbance caused by acoustic heterogeneity of the target in the environment; estimating a second distance between the source and target using the second time of receipt; obtaining a location of the target from the first and second estimated distances.

10 Claims, 3 Drawing Sheets

(52) U.S. Cl.
CPC ............... *A61B 5/0059* (2013.01); *A61B 8/00* (2013.01); *A61B 2576/00* (2013.01)

(56) References Cited

U.S. PATENT DOCUMENTS

| | | | |
|---|---|---|---|
| 9,405,000 B2* | 8/2016 | Yeh | G01S 5/16 |
| 9,901,281 B2* | 2/2018 | Ikushima | A61B 5/05 |
| 2010/0041987 A1 | 2/2010 | Manohar et al. | |
| 2011/0066030 A1* | 3/2011 | Yao | A61B 8/485 600/438 |
| 2012/0123256 A1* | 5/2012 | Razansky | A61B 5/0095 600/431 |
| 2012/0302866 A1 | 11/2012 | Fukutani et al. | |
| 2013/0101090 A1* | 4/2013 | Schubert | G01N 23/203 378/87 |
| 2013/0137960 A1* | 5/2013 | Lisogurski | A61B 5/0095 600/407 |
| 2013/0160558 A1* | 6/2013 | Oishi | A61B 5/0059 73/655 |
| 2015/0366458 A1* | 12/2015 | Kellnberger | A61B 5/0095 600/407 |
| 2016/0058296 A1* | 3/2016 | Da Silva | A61B 5/0093 600/407 |

OTHER PUBLICATIONS

International Search Report dated May 23, 2014 in PCT/FR2014/050679 filed Mar. 24, 2014.
French Search Report dated Oct. 28, 2013 in French Application No. 1354072 Filed May 2, 2013.
Li, C. et al., "Photoacoustic tomography and sensing in biomedicine", Phys Med Biol., vol. 54, No. 19, pp. 1-52, 2009.
Zalev, J. et al., "Clinical Feasibility Study of Combined Optoacoustic and Ultrasonic Imaging Modality Providing Coregistered Functional and Anatomical Maps of Breast Tumors", Proc. of SPIE, vol. 8223, pp. 82230A-1-82230A-6, 2012.

\* cited by examiner

METHOD AND DEVICE FOR LOCATING AT LEAST ONE TARGET IN AN ELECTROMAGNETICALLY ABSORBENT ENVIRONMENT

This invention relates to a method for locating at least one target in an electromagnetically absorbent environment. It also relates to a corresponding computer program and device, as well as an application of this method for detecting and locating tumors in biological tissues.

The invention applies more particularly to a method for locating at least one target in an electromagnetically absorbent environment, comprising the following steps:
- emitting at least one electromagnetic excitation signal from at least one source,
- receiving, by at least one acoustic sensor, an acoustic signal resulting from the emission of this excitation signal,
- detecting, in the received acoustic signal by the acoustic sensor, a time of receipt of a response to the excitation signal, this response resulting from an acoustic disturbance caused by an electromagnetic heterogeneity of the target in the environment, and
- estimating a distance between the target and the acoustic sensor using this time of receipt.

The context of the invention is therefore that of optoacoustic imagery, also referred to as photoacoustic, or thermoacoustic, applied to the locating of heterogeneities (or targets) embedded in an environment characterized by electromagnetic and acoustic properties that are different from these heterogeneities. This is for example the case of heterogeneities such as tumors in biological tissues.

The optoacoustic or thermoacoustic imagery is as such growing rapidly now in the biomedical field, in particular because it is deemed to be non-invasive and non-ionizing. Its principle is for example described in the article by C. Li and L. Wang, entitled "Photoacoustic tomography and sensing in biomedicine", published in Physics in Medicine and Biology, vol. 54, pages R59-R97, 2009.

The current techniques of optoacoustic or thermoacoustic imagery make use of the instantaneous generation of a local acoustic disturbance caused by an electromagnetic heterogeneity of a target in an electromagnetically absorbent and diffusing (from the standpoint of optoacoustic imagery) or diffracting (from the standpoint of thermoacoustic imagery) environment, when an electromagnetic excitation signal is emitted from a source. More precisely, the electromagnetic energy emitted, by being partially absorbed in the environment observed, is thermally dissipated, which creates dilatations in the environment. In particular, the electromagnetic heterogeneity of the target locally creates a dilatation heterogeneity which in turn generates the local acoustic disturbance that reveals this heterogeneity.

This local acoustic disturbance is detected on an acoustic sensor in the form of a response with a delay, in relation to the emission of the excitation signal, that is significant of the distance between the target and the acoustic sensor. This distance can therefore be estimated using the time of receipt of the aforementioned response by the acoustic sensor. Indeed, the optoacoustic or thermoacoustic imagery uses the property according to which the generating of the acoustic disturbance on the target is carried out from the source at a speed close to that of light (speed of electromagnetic propagation), or in any case very high compared to that of the sound in the environment, while the propagation of the acoustic disturbance from the target to the acoustic sensor is carried out at the speed of sound. Consequently, by synchronizing the receipt with the emission and by knowing the speed of the sound in the environment, the distance between the target and the acoustic sensor is simply deduced from the time that has elapsed between the emission of the excitation signal and the receipt of the response to this signal.

It is as such possible to locate the target in the three-dimensional space on a sphere of which the center is the acoustic sensor and of which the radius is the estimated distance. But several emissions-receipts are required in order to locate the target more precisely. As such the current technologies imply a certain complexity in the capturing and processing of signals in order to allow for a locating of the target. As furthermore these technologies are generally integrated into a more general principle of tomographic imagery, their complexity will also generate a greater complexity in tomographic reconstruction.

A solution is to combine the optoacoustic or thermoacoustic technology with for example a purely ultrasonic technology, in order to limit the number of emissions/receipts required. Such a solution is proposed in the article by J. Zalev et al, entitled "Clinical feasibility study of combined optoacoustic and ultrasonic imaging modality providing coregistered functional and anatomical maps of breast tumors", published in Photons Plus Ultrasound: Imaging and Sensing 2012, Proceedings of SPIE, vol. 8223, 2012. It remains technically complex since it combines two close but separate technologies.

Moreover, the current optoacoustic or thermoacoustic imagery technologies limit the use of the acoustic signal resulting from the emission of the excitation signal to the electromagnetic inhomogeneity of the target. In order to concentrate on this property, in particular when the environment wherein the target is located is itself acoustically inhomogeneous, it is even taught to overcome this problem by limiting the bandwidth of the acoustic sensor or by taking acoustic measurements in a geometric configuration perpendicular to the illumination of the environment. This is what is disclosed in the article by S. Ermilov et al, entitled "Laser optoacoustic imaging system for detection of breast cancer", published in the Journal of Biomedical Optics, vol. 14(2), pages 024007-1 to 024007-14, March/April 2009. However, other responses to the excitation signal are present in the signal received by the acoustic sensor and would probably warrant being used rather than having recourse to combinations of different technologies. As such for example, an electromagnetic inhomogeneity exists between the source of emission and the environment, but it is not used in the aforementioned documents of prior art.

However, in international patent application WO 2011/096198 A1, the electromagnetic inhomogeneity of the source with respect to the environment is used, more precisely its optical inhomogeneity. This leads to detecting, in addition to the response resulting from an acoustic disturbance caused by an electromagnetic heterogeneity of the target in the environment, another response resulting from an acoustic disturbance caused by the optical heterogeneity of the source with respect to the environment. This other response propagates at the speed of the sound in the environment, from the source to the acoustic sensor. By knowing the distance that separates the source from the acoustic sensor, an estimation of the speed of the sound in the environment is deduced from this. This solution therefore makes it possible to dispense with knowledge a priori of the speed of the sound in the environment in order to estimate the distance separating the target from the acoustic sensor.

But here again, several emissions-receipts are required in order to locate the target more precisely which makes this technology complex.

It can then be desired to provide a method for locating at least one target in an environment which makes it possible to overcome at least part of the aforementioned problems and constraints.

A method for locating at least one target in an electromagnetically absorbent environment is therefore proposed, comprising the following steps:

emitting at least one electromagnetic excitation signal from at least one source, receiving, by at least one acoustic sensor, an acoustic signal resulting from the emission of this excitation signal, detecting, in the received acoustic signal by the acoustic sensor, a first time of receipt of a first response to the excitation signal, this first response resulting from an acoustic disturbance caused by an electromagnetic heterogeneity of the target in the environment, estimating a first distance between the target and the acoustic sensor using this first time of receipt, further comprising the following characteristics:

detecting, in the same acoustic signal received by the acoustic sensor, a second time of receipt of a second response to the excitation signal, this second response resulting from an acoustic disturbance caused by an acoustic heterogeneity of the target in the environment, estimating a second distance between the source and the target using this second time of receipt, and obtaining a location of the target from the first and second estimated distances.

By using the acoustic heterogeneity of the target in the environment, a method for locating according to the invention makes it possible to improve the existing technologies very significantly. Indeed, this leads to detecting, in addition to the first response resulting from a first acoustic disturbance caused by the electromagnetic heterogeneity of the target in the environment, a second response resulting from a second acoustic disturbance caused by the acoustic heterogeneity of the target. The second acoustic disturbance is generated on the source and propagates, from the source to the target, at the speed of the sound in the environment, then continues to propagate, from the target to the acoustic sensor, also at the speed of the sound in the environment. Consequently, by synchronizing the receipt with the emission and by knowing the speed of the sound in the environment, the length of the source-target-sensor path is simply deduced from the time that has elapsed between the emission of the excitation signal and the receipt of the aforementioned second response. Knowing furthermore the distance between the target and the sensor thanks to the first response, the distance between the source and the target is deduced using the time of receipt of the second response. The distance between the source and the target can also be deduced directly using the time elapsed between the first and second times of receipt. As such, with a single emission, two pieces of information are available, the source-target distance and the target-sensor distance, in order to locate the target more precisely in the environment. At a constant number of emissions-receipts, better locating is thus obtained. Alternatively, for a desired locating precision of the target, it becomes possible to reduce the number of emissions-receipts.

Optionally:

the estimation of the distance between the target and the acoustic sensor is carried out by multiplying a first flight time of the first response between the target and the acoustic sensor by a predetermined value of the acoustic wave speed in the environment, the first flight time is estimated as being the elapsed time between the time of emission of the excitation signal and the first time of receipt.

Also optionally:

the estimation of the distance between the source and the target is carried out by multiplying a second flight time of the second response between the source and the target by the predetermined value of the acoustic wave speed in the environment, the second flight time is estimated as being the difference between, on the one hand, the elapsed time between the time of emission of the excitation signal and the second time of receipt, and, on the other hand, the first flight time.

Also optionally, the locating of the target in the three-dimensional space is obtained by intersection of two spheres, with the first sphere having as a center the acoustic sensor and as a radius the first distance, with the second sphere having the source as a center and the second distance as a radius.

Also optionally, the excitation signal emitted is an optical signal coming from a light source with a modulated frequency and/or intensity and the two responses to the excitation signal are pulse response resulting from two acoustic disturbances caused by a double optical and acoustic heterogeneity of the target in the environment.

Also optionally, a method for locating at least one target according to the invention can comprise the following steps:

emitting electromagnetic excitation signals from several sources distributed at the periphery of the environment wherein the target is located, receiving, by several acoustic sensors distributed at the periphery of the environment wherein the target is located, acoustic signals resulting from the emissions of these excitation signals, and tomographic reconstruction of an image of the target in the environment wherein it is located, using obtained locations of the target.

Also optionally, the sources and the acoustic sensors are distributed regularly on a circle around the environment in which the target is located.

An application of a method for locating at least one target according to the invention for detecting and locating tumors in biological tissues is also proposed.

A computer program is also proposed that can be downloaded from a communication network and/or recorded on a support that can be read by a computer and/or that can be executed by a processor, comprising instructions for the execution of the steps of a method for locating at least one target according to the invention, when said program is executed on a computer.

A device for locating at least one target in an electromagnetically absorbent environment is also proposed, comprising:

at least one source for emitting at least one electromagnetic excitation signal, at least one acoustic sensor of an acoustic signal resulting from the emission of this excitation signal, a calculator designed to detect, in the received acoustic signal by the acoustic sensor, a first time of receipt of a first response to the excitation signal, this first response resulting from an acoustic disturbance caused by an electromagnetic heterogeneity of the target in the environment, and to estimate a first distance between the target and the acoustic sensor using this first time of receipt, wherein the calculator is furthermore designed to:

detect, in the same received acoustic signal by the acoustic sensor, a second time of receipt of a second response to the excitation signal, this second response resulting from an acoustic disturbance caused by an acoustic heterogeneity of the target in the environment, estimate a second distance between the source and the target using this second time of receipt, and provide a locating of the target from the first and second estimated distances.

Figure 2:
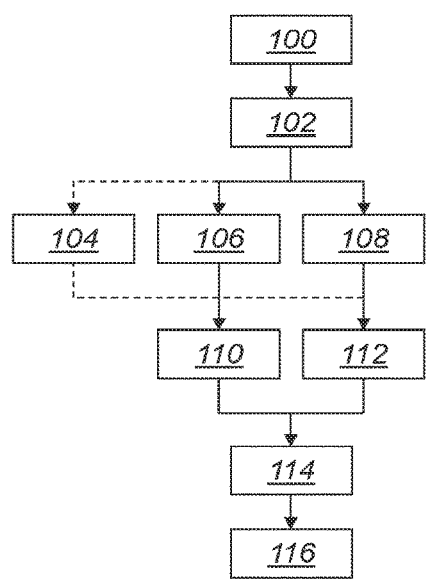
Figure 3:
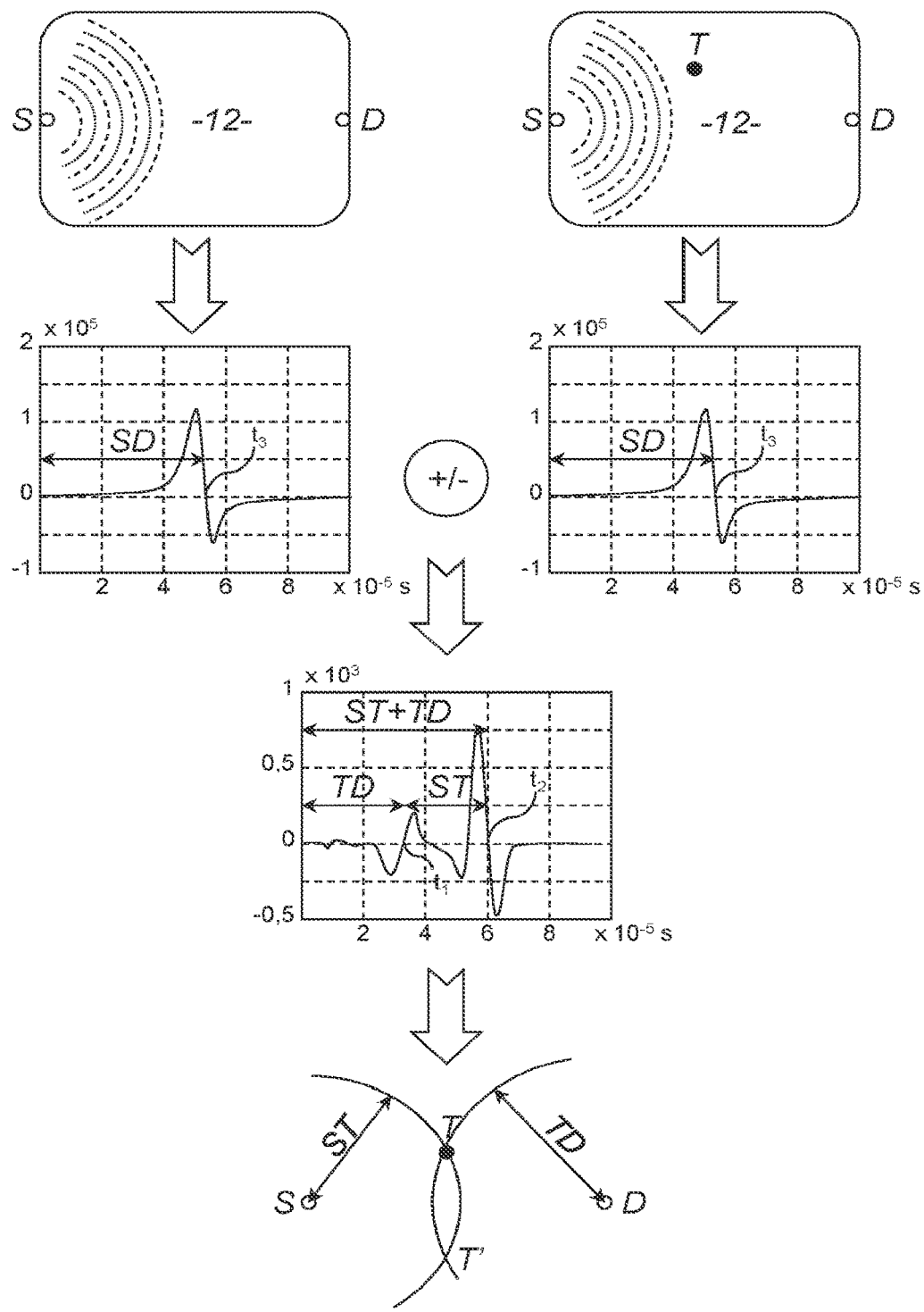
Figure 4:
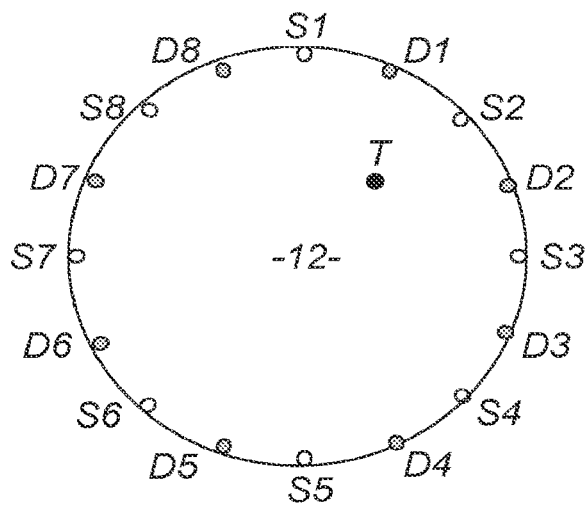
Figure 5:
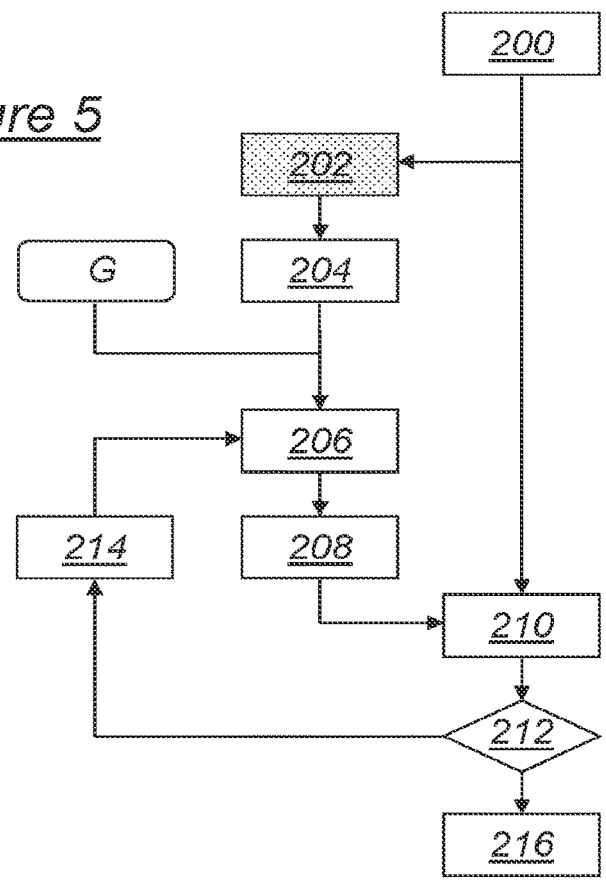

The invention will be better understood using the following description, provided solely as an example and made in reference to the annexed drawings wherein:

FIG. 1 diagrammatically shows the general structure of a device for locating a target in an electromagnetically absorbent environment, according to an embodiment of the invention, FIG. 2 shows the successive steps of a method implemented by the device of FIG. 1, FIG. 3 shows an example of an application of the method of FIG. 2, FIG. 4 diagrammatically shows the general structure of an example of a emission/receipt system for the device of FIG. 1, and FIG. 5 shows the integration of the method of FIG. 2 into a more global diagram of tomographic reconstruction by optoacoustic or thermoacoustic imagery.

In what follows, we shall consider the optoacoustic (or photoacoustic) field in a purely illustrative and non-restricted manner.

The device 10 shown diagrammatically in FIG. 1 is as such a device for optoacoustic imagery that allows for the locating of at least one target T located in an environment 12 that is optically absorbing and diffusing (since optoacoustic imagery is considered). The target T, for example a tumor in the environment observed 12 constituted of a biological tissue, has a double optical and acoustic heterogeneity in the environment 12 which is moreover homogeneous from the standpoint of these two characteristics. This double heterogeneity of the target T is used by the device 10 to allow it to be located, and possible to be viewed.

For this purpose, the device for locating 10 comprises an emitter 14 comprising at least one source of emitting at least one electromagnetic excitation signal E, more precisely optical in this example. This emitter 14 is designed to optically illuminate the environment 12 and generate acoustic disturbances caused by the double optical and acoustic heterogeneity of the target T in its environment 12 and by the optical heterogeneity of the source of emission with respect to the environment 12. As such, in a manner known per se and according to the general principles of optoacoustic imagery, the emitter 14 is a light source with a modulated frequency and/or intensity, for example a pulsed laser emitter of the Nd:Yag type at 1064 nm, with a laser pulse temporal width of about 3 ns, having a rate of repetition of 10 Hz and a power less than 20 mJ/cm$^2$ if the environment 12 is a biological tissue. In light of the optical properties of the environment 12, there is the instantaneous creation, i.e. at a speed close to that of light or in any case very high before that of the sound in the environment 12, a CPinit map of the distribution of the initial pressure in the environment 12 that reveals the dilatations mentioned hereinabove. This distribution of initial pressure then generates an acoustic pressure wave that propagates at the speed of the sound according to the acoustic properties of the environment 12. If elements in the environment, such as the target T, are optically and acoustically inhomogeneous, acoustic disturbances corresponding to these heterogeneities can be detected by receipts of acoustic signals resulting from the emission of the excitation signal E.

The device for locating 10 therefore furthermore comprises a receiver 16 comprising at least one acoustic sensor of an acoustic signal R resulting from the emission of the excitation signal E. The acoustic sensor or sensors of the receiver 16 are well known to those skilled in the art and details of them will not be provided. One can in particular refer to the documents of prior art mentioned hereinabove.

The device for locating 10 further comprises an acquisition card 18 allowing for a pre-processing of the received signal R, for example a filtering and a digitizing, as well as a synchronizing of the pre-processed signal using a "sync" signal received from the emitter 14. The received signal R indeed comprises a certain number of acoustic pulse responses to each optical pulse emitted by the emitter 14, with each of these pulse responses being, as details will be provided in what follows, caused by an electromagnetic heterogeneity, more precisely optical in this example, in the environment 12. It is therefore important to synchronize the received signal R with respect to the excitation signal E in order to allow for an estimation of the times of receipt of the acoustic pulse responses that can be detected in the received signal R in relation to the time of emission of the excitation signal E.

The device for locating 10 further comprises a calculator 20 programmed to control the emitter 14 using a signal C according to a desired illumination of the environment 12 and in order to analyze the signal received by the receiver 16 and pre-processed by the acquisition card 18. This received and pre-processed signal is noted as Rs at the output of the acquisition card 18.

The calculator 20 such as shown diagrammatically in FIG. 1, comprises a processing unit 22 conventionally associated with a memory 24 (for example a RAM memory).

The processing unit 22 can for example be implemented in an IT device such as a conventional computer comprising a processor associated with one or several memories for the storage of data files and of computer programs. The processing unit 22 can then itself be considered as formed of this processor associated with the memory 24 acting as memory for the storage of the instructions that the processor executes in the form of computer programs.

The memory 24 such as shown in FIG. 1 as such functionally comprises two computer programs or two functions of the same computer program 26 and 28. Note indeed that the computer programs 26 and 28 are presented as being separate, but this distinction is purely functional. They can just as well be grouped together according to all of the possible combinations into one or several pieces of software. Their functions could also be at least partially microprogrammed or micro-wired in dedicated integrated circuits. As such, as an alternative, the IT device implementing the calculator 20 could be replaced with an electronic device comprised solely of digital circuits (without a computer program) in order to perform the same actions.

The first computer program 26 comprises instructions for the execution of a generation of the signal C by the processing unit 22. This type of computer program is well known and details will not be provided.

The second computer program 28 comprises instructions for the execution of an analysis of the signal Rs by the processing unit 22. More precisely, these instructions are designed to detect, through an analysis of the signal Rs:
- a first time $t_1$ of receipt of a first response to the excitation signal E, with this first response resulting from a first acoustic disturbance caused by the optical heterogeneity of the target T in the environment 12,
- a second time $t_2$ of receipt of a second response to the excitation signal E, with this second response resulting from a second acoustic disturbance caused by the acoustic heterogeneity of the target T in the environment 12, and possibly
- a third time $t_3$ of receipt of a third response to the excitation signal E, with this third response resulting from a third acoustic disturbance caused by the optical heterogeneity of the source of emission of the excitation signal E with respect to the environment 12.

The optional detection of the third time $t_3$ is for example carried out in accordance with the teaching of aforementioned document WO 2011/096198 A1. It makes it possible to determine, with knowledge a priori of the distance noted as SD between the source of emission of the excitation signal E and the sensor of the acoustic signal R, what is the average propagation speed v of an acoustic wave in the environment 12. By noting $t_0$ as the time of emission of the excitation signal E, the speed v can be estimated using the following relationship:

$$v = \frac{SD}{t_3 - t_0}.$$

Alternatively, the speed v can be considered as known a priori, in such a way that estimating it is not required.

The detecting of the first time $t_1$ is carried out in accordance with the teaching of document WO 2011/096198 A1 or of other documents of prior art mentioned hereinabove. The property, according to which the generating of the first acoustic disturbance on the target is carried out from the source at a speed close to that of light while the propagation of the acoustic disturbance from the target to the acoustic sensor is carried out at the speed of the sound, is then used in order to perform the following calculation:

$$TD = v \cdot (t_1 - t_0), \text{ or } TD = \frac{SD}{t_3 - t_0} \cdot (t_1 - t_0),$$

where TD is the distance between the target T and the sensor of the acoustic signal R. It is indeed considered with a very good approximation that the first acoustic disturbance is generated on the target T at the time $t_0$ while the acoustic response that it generates is received by the sensor of the acoustic signal R at the time $t_1$.

The detecting of the second time $t_2$ is carried out in contradiction with the teaching of the documents of prior art mentioned hereinabove. None of these documents uses the property according to which a disturbance (i.e. the aforementioned second disturbance) is generated on the target due to its acoustic heterogeneity in the environment 12. Worse, certain documents of prior art even teach to filter the acoustic signal R in such a way as to suppress, among others, this second disturbance, in order to suppress the effect of the acoustic inhomogeneities in the environment 12 generally perceived as an artifact to be removed. On the contrary and in accordance with the invention, the property, according to which the generating of the second acoustic disturbance on the target is carried out from the source at the speed of the sound and then propagates from the target to the sensor also at the speed of the sound, is used in order to perform the following calculation:

$$ST + TD = v \cdot (t_2 - t_0),$$

where ST is the distance between the source of emission of the excitation signal E and the target T. The second acoustic disturbance is indeed generated on the source at the time $t_0$ while the acoustic response that it generates is received by the sensor of the acoustic signal R at time $t_2$.

An expression of the distance ST is deduced from the two preceding calculations:

$$ST = v \cdot (t_2 - t_1), \text{ or } ST = \frac{SD}{t_3 - t_0} \cdot (t_2 - t_{e1}).$$

Consequently, after having detected the times $t_1$, $t_2$ and possibly $t_3$, the instructions of the second computer program 28 are designed to:
- estimate the distance TD between the target and the receiving sensor of the acoustic signal R using the first time of receipt $t_1$, and possibly the third time of receipt $t_3$ if the speed v is not known, according to the calculation for which the details were provided hereinabove,
- estimate the distance ST between the source of emission of the excitation signal E and the target using the first time of receipt $t_1$, the second time of receipt $t_2$, and possibly the third time of receipt $t_3$ if the speed v is not known, according to the calculation for which the details were provided hereinabove,
- provide a location of the target using the distances ST and TD estimated hereinabove.

The supplying of the location is generally carried out in the three-dimensional space by the intersection of two spheres, with the first sphere having as a center the receiving sensor of the acoustic signal R and as a radius the distance TD, with the second sphere having as a center the source of emission of the excitation signal E and as a radius the distance ST. This can be done more precisely and advantageously in a plane of illumination of the environment 12, with the intersection of the two spheres as such becoming an intersection of two circles. With these two circles having a priori two points of intersection, there remains a doubt as to the location of the target T. This doubt can be lifted using another emission/receipt or more simply using geometrical considerations, for example if one of the two points is located outside of the environment observed 12. As such, in a plane, the locating of the target can be resolved without ambiguity using a single emission of excitation signal E. However, in the three-dimensional space, an additional emission may be necessary in order to resolve the location without ambiguity by the intersection of three spheres. Note furthermore that environments with acoustic heterogeneities induce an incoherency of estimated positions: the uncertainty on a global position can however be minimized by multiplying the angles of examination of the environment observed 12.

A method for locating the target T in the environment 12 implemented by the device 10 described hereinabove will now be detailed in reference to FIG. 2.

During a first step of emission 100, the optical excitation signal E is emitted at time $t_0$ from a source S of the emitter 14 upon receipt by the latter of the control signal C emitted by the processing unit 22 of the calculator 20.

During a following step of receiving 102, the acoustic signal R resulting from this emission is received, from the time $t_0$ and at least to the times $t_1$, $t_2$ and possibly $t_3$, by a sensor D of the receiver 16 then pre-processed by the acquisition card 18 which transmits the pre-processed acoustic signal Rs to the processing unit 22 of the calculator 20.

During an optional step of detecting 104 following the step 102, the third time $t_3$ is detected by execution of the second computer program 28. The principle of this detection will be detailed in reference to FIG. 3.

During a step of detecting 106 following the step 102, the first time $t_1$ is detected by execution of the second computer program 28. The principle of this detection is the same as that of the optional step 104.

During a step of detecting 108 following the step 102, the second time $t_2$ is detected by execution of the second computer program 28. The principle of this detection is the same as that of the optional step 104.

During a step of estimating 110 following the step 106, and possibly the optional step 104 where applicable, the distance TD between the target T and the acoustic sensor D is estimated by execution of the second computer program 28 according to the calculation for which the details were provided hereinabove.

During a step of estimating 112 following the step 108, and possibly the optional step 104 where applicable, the length ST+TD is estimated by execution of the second computer program 28 according to the calculation for which the details were provided hereinabove.

During a step of estimating 114 following the steps 110 and 112, the distance ST between the source S and the target T is estimated by execution of the second computer program 28 by subtraction of TD from the length ST+TD. Alternatively, instead of proceeding with the calculation in two steps 112 and 114, note that the distance ST can be calculated directly using times $t_1$ and $t_2$ (and possibly $t_3$) according to the calculation for which the details were provided hereinabove.

Finally, during a last step of locating 116, a geometrical locating of the target T by the intersection of spheres or of circles is obtained by execution of the second computer program 28, using estimated distances ST and TD. Optionally and as an alternative, other algorithms for tomographic reconstruction can be used such as for example a method of adding filtered retroprojections or any known algebraic method.

In the example shown in FIG. 3, the method of FIG. 2 implemented by the device 10 of FIG. 1 is applied with a single source S of emission of the excitation signal E and a single acoustic sensor D for reasons of simplicity.

In the upper left part of FIG. 3, the steps 100, 102 and 104 are applied to the environment 12 without the target T. The signal Rs obtained has a response of the pulse form wherein the time $t_3$ is detected in the following way. This time is chosen as corresponding to the passage at zero of the pulse response, with the latter having an upper peak followed by a lower peak. In the particular and experimental example shown in FIG. 3, the time $t_3$ is detected at $5.39 \cdot 10^{-5}$ s, with the origin of the times being chosen at $t_0$. For a speed of sound v=1485 m/s, SD≈8 cm is deduced. In practice, it is rather the inverse calculation that is performed. Knowing for example a priori the distance SD of 8 cm between the source S and the sensor D, the value at 1485 m/s of the speed of the sound in the environment 12 is deduced thanks to the detection of $t_3 = 5.39 \cdot 10^{-5}$ s.

In the upper right part of FIG. 3, the steps 100, 102 and 104 are applied to the environment 12 with the target T. The signal Rs obtained still has a response of the pulse form wherein the time $t_3$ can be detected in the same way as beforehand. But, in the example shown, the pulse responses caused by the optical and acoustic inhomogeneities of the target T cannot be seen, as the latter are of amplitudes that are very largely less than that caused by the optical inhomogeneity of the source.

It is therefore advantageous in this example to proceed with a subtraction between the two signals Rs obtained in the right and left part of FIG. 3. Concretely, in an application of detecting and locating a tumor in a biological tissue, it is sufficient to have reference signals Rs concerning a healthy tissue that is suitable to subtract from the signals captured for a biological tissue to be tested.

In certain applications and according to the contrasts of optical and acoustic properties between the environments, the three pulse responses can be seen on the same acoustic signal in such a way that a subtraction with a reference signal is not always required. But it is however generally required for applications for observing thick biological tissues.

In the example shown, after the aforementioned subtraction, the signal Rs shown in the lower part of FIG. 3 is obtained. Two pulse responses corresponding respectively to the times $t_1$ and $t_2$ are now easily visible. The first one, corresponding to the time $t_1$, has a lower peak followed by an upper peak between which the passage at zero determines the time $t_1$. In the particular and experimental example shown in FIG. 3, the time $t_1$ is detected at $3.39 \cdot 10^{-5}$ s, with the origin of the times being chosen at $t_0$. For a speed of sound v=1485 m/s, TD≈5 cm is deduced. The second pulse response, corresponding to the time $t_2$, has an upper peak followed by a lower peak between which the passage at zero determines the time $t_2$. In the particular and experimental example shown in FIG. 3, the time $t_2$ is detected at $6.07 \cdot 10^{-5}$ s, with the origin of the times being chosen at $t_0$. For a speed of sound v=1485 m/s, ST≈4 cm is deduced.

Finally, via geometrical reconstruction (intersection of two spheres brought to an intersection of two circles if a plane is considered), the locating of the target T is identified, possibly with an uncertainty, between two locations T and T'. As indicated hereinabove, this uncertainty can be resolved for example if T' is geometrically located outside of the environment 12.

As shown in FIG. 4, for imagery applications via tomographic reconstruction, the emitter/receiver unit 14, 16 can comprise several sources and several acoustic sensors. The environment 12 observed is for example in the shape of a disk and several sources S1, S2, S3, S4, S5, S6, S7, S8 are distributed regularly on a circle at the periphery of this disk. Likewise, several acoustic sensors D1, D2, D3, D4, D5, D6, D7, D8 are distributed regularly on a circle at the periphery of this disk, inserted between the sources. Thanks to this configuration of the emitter/receiver unit 14, 16, an optoacoustic tomographic reconstruction of an image of the target T in the environment 12 wherein it is located can be performed, using obtained locations of the target T by successive emissions/receipts carried out using these multiple sources and sensors.

An example of the method of imagery via tomographic reconstruction that integrates a method for locating according to the invention is shown in FIG. 5.

During a step 200, a set of measurements by successive emissions/receipts is carried out using optical sources and acoustic sensors of the emitter 14 and of the receiver 16.

During a step 202 following the step 200, the steps 100 to 116 of the method of FIG. 2 are executed for each emission/ receipt in such a way as to provide a precise location of the target T in the environment 12.

During a step 204 following the step 202, the CPinit map for the distribution of the initial pressure in the environment 12 is established by simulation of the illumination of the environment 12 by the optical sources of the emitter 14, with this simulation integrating, in accordance with the invention, the locating of the target T such as estimated in the step 202.

Using geometrical information G on the optical sources of the emitter 14, on the acoustic sensors of the receiver 16 and on the outside contours of the illuminated environment 12, a complete model of this environment 12 including the target T is established during the step 206. Optionally and more generally, any information a priori (morphology, average physical or physiological parameters, etc.) can be used in order to establish this model.

The measurements taken during the step 200 are simulated on the model established in the step 206 during a following step 208.

The measurements simulated during the step 208 are compared with the actual measurements of the step 200 during a step 210. This comparison is carried out in a manner known per se by minimizing an error function, for example a quadratic error.

During a following step of testing 212, the error function is compared with a predetermined threshold $\varepsilon$. If it remains greater than this threshold, the method passes to a step 214 of revising the CPinit map for the distribution of the initial pressure. Otherwise, the method passes to a step 216 of recording, and possibly of displaying, an image that represents the environment 12 with the target T correctly located, with this image being defined based on the model established in the step 206.

During the step 214, the revising of the CPinit map for the distribution of the initial pressure is carried out in a manner known per se by optimizing the error function. At the end of this step, the method resumes at the step 206 in such a way as to update the previously established model according to the CPinit map for the distribution of the initial pressure such as revised in the step 214.

It clearly appears that a device and a method for locating such as those described hereinabove make it possible to more effectively locate a target in an environment illuminated by an optoacoustic technology. In particular, the principles of detection proposed make it possible to overcome a combining of different technologies in order to arrive at a precise location, then a representing, of targets in an environment. They make optimum use of the acoustic signals received in response to the optical excitations emitted, by taking advantage of the properties of optical but also acoustic inhomogeneities of the targets to be detected.

The results are particularly convincing in the field of medical imagery, for the detecting of tumors in biological tissues. Furthermore, in medical imagery, the application of a method for locating according to the invention is compatible with the use of contrast agents such as in the other conventional technologies.

Note moreover that the invention is not limited to the embodiments described hereinabove.

In particular, the description more precisely covered the implementing of the invention in the context of an optoacoustic acquisition technology. But it is quite obvious that its principles can be adapted simply and in a manner known per se by those skilled in the art to a thermoacoustic acquisition technology, in particular because the hypothesis of the much faster propagation of electromagnetic waves in the environment compared with that of the sound is also verified in thermoacoustic technology.

In fact, thermoacoustic technology, like optoacoustic technology, uses emitters of electromagnetic waves and acoustic receivers. What primarily distinguishes these two technologies, are the properties, of diffusion or diffraction, used of the environment observed according to the emitted wavelengths. When the emitted wavelengths generate a phenomenon of diffusion in the environment, it is the equation of radiative transfer (called RTE equation) that applies and which is used by optoacoustic technology. When the emitted wavelengths generate a phenomenon of diffraction in the environment, it is Maxwell equations that are applied and which are used by thermoacoustic technology. Generating a phenomenon of diffusion or of diffraction is a question of the size of the constituents of the environment observed in relation to the emitted wavelengths. As such for example, when it is desired to observe an environment comprised of a biological tissue, optoacoustic technology applies if the emitter emits waves in the visible and near-infrared light spectrum, since then the environment is diffusing, and thermoacoustic technology applies if the emitter emits microwaves, as then the environment is diffracting. When it is desired to observe an environment comprised of a transparent manufactured material, thermoacoustic technology applies if the emitter emits waves in the visible light spectrum, as then the environment is diffracting.

More precisely, the transposition of the teaching detailed hereinabove for thermoacoustic technology is carried out based on the following considerations:
- the environment to be observed is diffracting and not diffusing,
- with regards to the emission of excitation signals, the correct range of wavelengths must be considered according to the nature of the environment observed in such a way as to generate the phenomenon of diffraction that can be used in thermoacoustic technology, for example the range of microwaves for examining biological tissues and the range of visible light waves for examining transparent materials,
- the electromagnetic contrasts are with a local variation of dielectric proprieties, by variation in the real and imaginary parts of the permittivity and conductivity constants of the environment observed, in such a way that only the propagation equations change,
- the equations that govern the map for the initial distribution of pressure are Maxwell equations, not the RTE radiative transfer equation.

It will appear more generally to those skilled in the art that various modifications can be made to the embodiments described hereinabove, in light of the teaching which has just been disclosed. In the claims that follow, the terms used must not be interpreted as limiting the claims to the embodiments disclosed in this description, but must be interpreted to include therein all of the equivalents that the claims aim to cover due to their formulation and for which prevision is within the scope of those skilled in the art by applying the general knowledge to the implementing of the teaching that has just been disclosed.

The invention claimed is:

1. A method for locating at least one target in an electromagnetically absorbent environment, comprising:
   emitting at least one electromagnetic excitation signal from at least one source;
   receiving, by at least one acoustic sensor, an acoustic signal resulting from the emitting the excitation signal;

detecting, in the received acoustic signal by the acoustic sensor, a first time of receipt of a first response to the excitation signal, the first response resulting from an acoustic disturbance caused by an electromagnetic heterogeneity of the target in the environment;
estimating a first distance between the target and the acoustic sensor using the first time of receipt;
detecting, in the same received acoustic signal by the acoustic sensor, a second time of receipt of a second response to the excitation signal, this second response resulting from an acoustic disturbance caused by an acoustic heterogeneity of the target in the environment;
estimating a second distance between the source and the target using the second time of receipt; and
obtaining a location of the target from the first and second estimated distances.

2. The method for locating at least one target according to claim 1, wherein:
the estimating of the first distance between the target and the acoustic sensor includes multiplying a first flight time of the first response between the target and the acoustic sensor by a predetermined value of acoustic wave speed in the environment;
the first flight time is estimated as elapsed time between a time of emission of the excitation signal and the first time of receipt.

3. The method for locating at least one target according to claim 2, wherein:
the estimating of the second distance between the source and the target includes multiplying a second flight time of the second response between the source and the target by the predetermined value of the acoustic wave speed in the environment;
the second flight time is estimated as a difference between the elapsed time between time of emission of the excitation signal and the second time of receipt, and the first flight time.

4. The method for locating at least one target according to claim 1, wherein the location of the target in three-dimensional space is obtained by intersection of first and second spheres, with the first sphere having as a center the acoustic sensor and as a radius the first distance, with the second sphere having the source as a center and the second distance as a radius.

5. The method for locating at least one target according to claim 1, wherein the excitation signal emitted is an optical signal coming from a light source with a modulated frequency and/or intensity and the acoustic signal resulting from the excitation signal are pulse response resulting from two acoustic disturbances caused by a double optical and acoustic heterogeneity of the target in the environment.

6. The method for locating at least one target according to claim 1, further comprising:
emitting electromagnetic excitation signals from plural sources distributed at a periphery of the environment wherein the target is located;
receiving, by plural acoustic sensors distributed at the periphery of the environment wherein the target is located, acoustic signals resulting from the emissions of the excitation signals; and
tomographic reconstruction of an image of the target in the environment wherein it is located, using obtained locations of the target.

7. The method for locating at least one target according to claim 6, wherein the sources and the acoustic sensors are distributed regularly on a circle around the environment wherein the target is located.

8. An application of a method for locating at least one target according to claim 1 for detecting and locating tumors in biological tissues.

9. A non-transitory computer readable medium including computer executable instructions that can be read by a computer and/or that can be executed by a processor, comprising instructions for execution of the method for locating at least one target according to claim 1, when executed on a computer.

10. A device for locating at least one target in an electromagnetically absorbent environment, comprising:
at least one source for emitting at least one electromagnetic excitation signal;
at least one acoustic sensor of an acoustic signal resulting from the emitting of the excitation signal;
a calculator configured to detect, in the received acoustic signal by the acoustic sensor, a first time of receipt of a first response to the excitation signal, the first response resulting from an acoustic disturbance caused by an electromagnetic heterogeneity of the target in the environment, and to estimate a first distance between the target and the acoustic sensor using this first time of receipt;
the calculator further configured to:
detect, in the same received acoustic signal by the acoustic sensor, a second time of receipt of a second response to the excitation signal, the second response resulting from an acoustic disturbance caused by an acoustic heterogeneity of the target in the environment;
estimate a second distance between the source and the target using the second time of receipt; and
provide a locating of the target from the first and second estimated distances.

* * * * *